US00PP09983P

United States Patent [19]

Corley

[11] Patent Number: Plant 9,983

[45] Date of Patent: Jul. 29, 1997

[54] *RHAPHIOLEPIS DELACOURII* 'GEORGIA PETITE'

[75] Inventor: Will L. Corley, Griffin, Ga.

[73] Assignee: University of Georgia Research Foundation, Inc., Athens, Ga.

[21] Appl. No.: 542,633

[22] Filed: Oct. 13, 1995

[51] Int. Cl.[6] ..... A01H 5/00

[52] U.S. Cl. ..... Plt./67.5

[58] Field of Search ..... Plt./54.1, 67.5

[56] References Cited

U.S. PATENT DOCUMENTS

P.P. 9,398 12/1995 Berry ..... Plt./67.5

OTHER PUBLICATIONS

Everett, Thomas H., "The New York Botanical Garden Illustrated Encyclopedia of Horticulture," 1992, Garland Publishing, Inc., pp. 2885–2886.

Lindstrom, Orville M. and Will L. Corley, "Leaf and Stem Cold Hardiness of Four Selections *Raphiolephis umbellata* Makino," 1992, J. Environ. Hort., 10(1):1–3.

"The New Royal Horticultural Society Dictionary of Gardening," Anthony Huxley, Editor–in–Chief, 1992, The MacMillan Press Limited, p. 24.

"The Hillier Manual of Trees and Shrubs, Sixth Edition," David & Charles, 1991, p. 356.

Odenwald, Neil G. and James R. Turner, "Plants for the South: A Guide for Landscape Design," 1980, Claitor's Publishing Division, Baton Rouge, p. 426.

Halfacre, R. Gordon, and Anne R. Shawcroft, "Landscape Plants of the Southeast," 1979, Sparks Press, p. 128, p. 88 and map.

*Primary Examiner*—James R. Feyrer

*Attorney, Agent, or Firm*—Greenlee, Winner and Sullivan, P.C.

[57] ABSTRACT

This new plant is a distinct variety of *Rhaphiolepis*× *delacourii* Andre that is characterized by its dwarf habit, its cold tolerance and its resistance to Entomosporium leafspot.

1 Drawing Sheet

FIELD OF THE INVENTION

The plant of this invention is an ornamental evergreen dwarf flowering shrub which is resistant to Entomosporium leafspot and is fairly cold hardy in comparison with other plants within the botanical and market classes.

BACKGROUND OF THE INVENTION

Rhaphiolepis is a genus of the Rosaceae family containing several species of evergreen shrubs that originated in China and Japan. They are considered well adapted for garden and landscape use in mild climate regions, and they are particularly well-suited to coastal areas, due to their tolerance to salt spray, drought and sandy soils.

The hybrid *Rhaphiolepis taxa, R.*×*delacourii,* was first reported and grown in the late nineteenth century by Delacour, gardener in Cannes, France. This hybrid selection shows moderate resistance to leaf spot and cold damage, while plant characters are intermedite between the parent species, *R. indica* and *R. umbellata. Rhaphiolepis umbellata* (sometimes referred to as *Rhaphiolepis japonica* or *Rhaphiolepis ovata*), commonly known as Yeddo Hawthorn, is native to Japan and the Ryukyu islands. It is typically a rounded shrub that can reach a maxiumu height of about 12 feet (The New York Botanical Garden Illustrated Encyclopedia of Horticulture, Thomas H. Everett, Garland Publishing, Inc. 1992, pp. 2885–2886).

*Rhaphiolepis umbellata* is used in the landscapes as an intermediate sized shrub. It is attractive because it blooms profusely in the springtime with white to pink flowers and because dark-blue to black fruits form in the summer and persist throughout the fall and winter. Regarding its size, it is typically reported as "unpredictable," with reports ranging from the 12 feet as reported above, to "4–6 feet, spread 6 feet" (in "Landscape Plants of the Southeast," R. Gordon Halfacre and Anne R. Shawcroft, Sparks Press 1979, p. 128), to "1–4 m" (in "The New Royal Horticultural Society Dictionary of Gardening," Anthony Huxley, Editor-in-Chief, The MacMillan Press Limited, 1992; p. 24) to "1.2 m" (in "The Hillier Manual of Trees & Shrubs, Sixth Edition," David & Charles, 1992, p. 356). Due to this documented variability in size, there has been a need to develop a new cultivar with a more compact habit for use in certain landscape settings. Additionally, there is a need to develop a landscape plant well-adapted to United States Department of Agriculture (USDA) Hardiness Zone 7b and which demonstrates resistance to leaf spot disease that has become a serious problem on this species.

ORIGIN OF THE INVENTION

'Georgia Petite' was developed from an organized, scientifically designed breeding program conducted at the University of Georgia Experiment Station at Griffin, Ga. 'Georgia Petite' originated from a seedling population of a cross of Plant Introduction selection *Rhaphiolepis umbellata* PI277653 and *Rhaphiolepis umbellata* 'Ovata.' The PI parent (currently available in the trade as 'Eskimo') has plant characters atypical of *R. umbellata,* being an apparent hybrid of *R. umbellata* and *R. indica,* consequently this accession more appropriately fits the description of *Rhaphiolepis*× *delacourii.* The two parents were chosen following a six-year study of twenty cultivars which were evaluated for cold tolerance and resistance to *Entomosporium maculatum* leafspot. These two parents were ranked the best in these two categories. Approximately 2,000 seedlings from the cross were grown in simulated nursery and landscape conditions and then evaluated for superiority in the desired characteristics of compact growth habit, cold tolerance, and leaf spot resistance. The first act of asexual reproduction of 'Georgia Petite' occurred in 1983 using semi-hardwood cuttings. Propagation has been successful (75 to 90 percent) using semi-hardwood cuttings taken during June to August. Cuttings were stuck in a well-drained medium under intermittent mist after a quick dip of 10,000 ppm IBA. Seeds are viable, but vegetative propagation is essential to maintain the characteristics true to the cultivar.

Plants are presently being propagated by four Georgia nursery propagators who were selected and licensed by the Georgia Seed Development Commission, Georgia Department of Agriculture.

SUMMARY OF THE INVENTION

The present invention comprises a new and distinct plant cultivar of *Rhaphiolepis×delacourii* Andre, which has been given the cultivar name 'Georgia Petite'.

The following are the most pronounced characteristics of this new cultivar when grown in the Georgia piedmont under low maintenance landscape conditions:

1. Very compact and mounding in nature. The plant is slightly wider than tall (2.5 feet×3.3 feet).

2. Moderately slow growth rate, self-shaping, requiring little pruning.

3. Cold hardy through USDA Zone 7b.

4. High resistance to leaf spot.

5. Relatively pest resistant.

6. Adapted to a wide range of soil types.

7. Mature leaves are dark green with light green undersides, obovate shape, serrate margins, and rounded apex.

8. Flowers are single, light pink at opening, fading to white at maturity.

9. Clusters of bluish-black fruits, one centimeter in diameter, persist from summer into winter.

10. Compactness of the plant obscures fruits borne by the precocious blooming traits.

11. Good plant for foundation plantings, informal beds, low hedges, ground cover and wildlife habitat.

BRIEF DESCRIPTION OF THE PHOTOGRAPHIC DRAWINGS

The file of this patent contains at least one drawing executed in color. Copies of this patent with color drawing (s) will be provided by the Patent and Trademark Office upon request and payment of the proper fee.

The accompanying photographic prints illustrate this new cultivar of *Rhaphiolepis×delacourii:*

Figure 1:
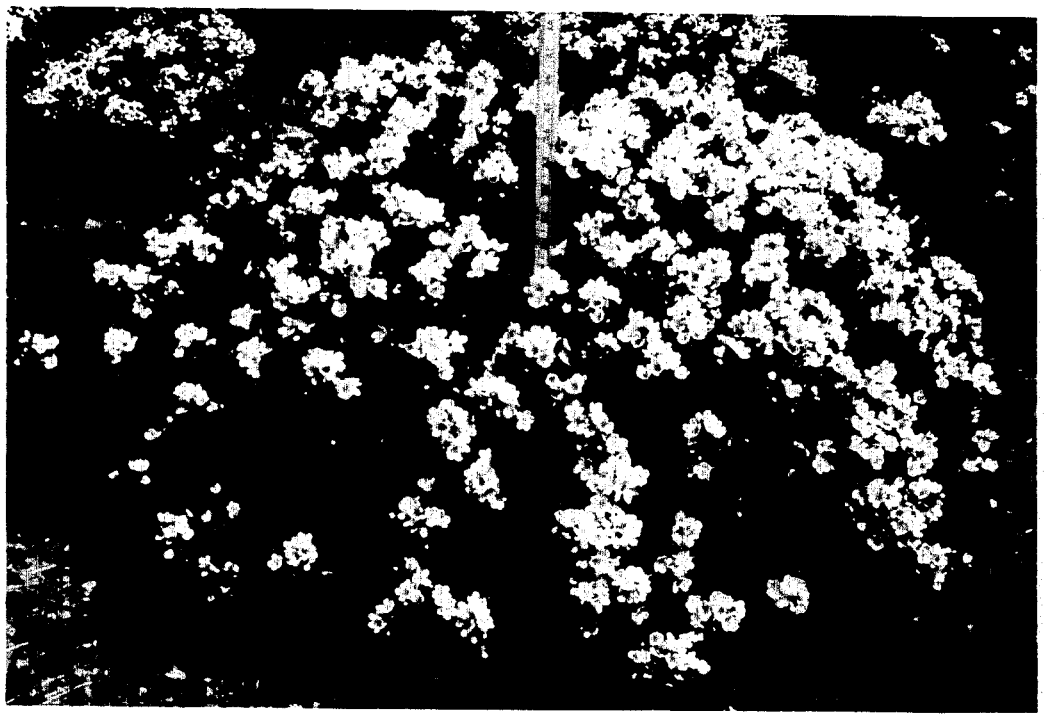
FIG. 1 illustrates the low stature of the plant relative to a yardstick.
Figure 2:
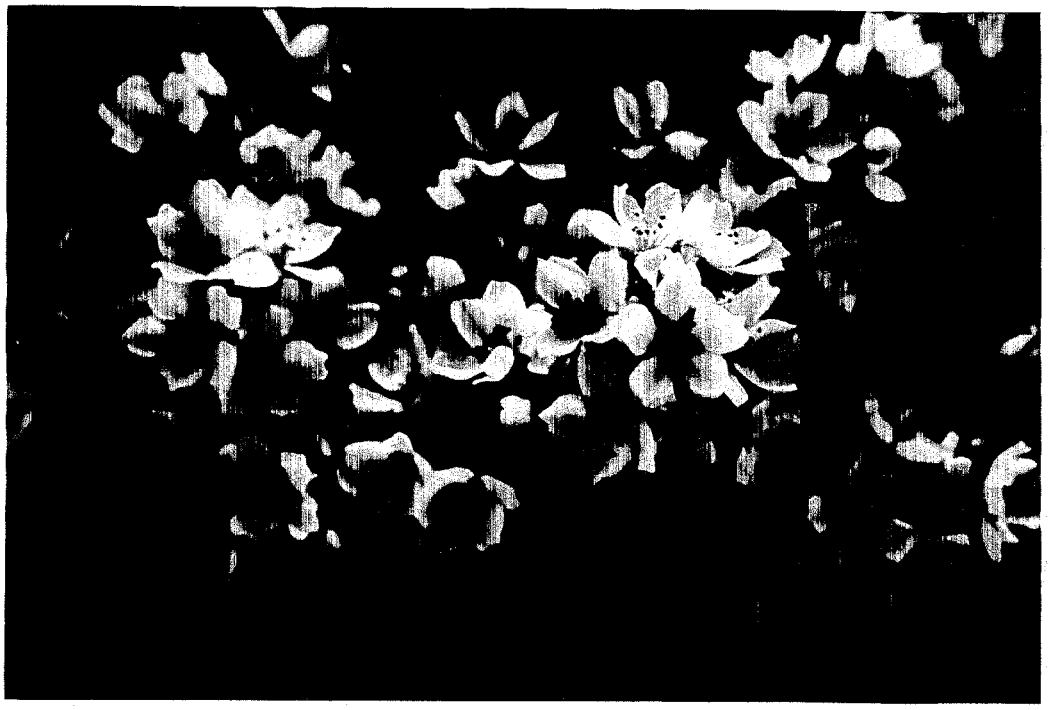
FIG. 2 illustrates the color and shape of the flowers and leaves of the plant in greater detail.

Colors shown are reasonably accurate by conventional photographic procedures. Colors of various plant parts are defined using The Royal Horticultural Society (R.H.S.) Colour Chart for standardization. Description of some colors in less exacting terms are used where appropriate for clarity in meaning.

BOTANICAL DESCRIPTION OF THE PLANT

'Georgia Petite' is a new and distinct plant cultivar of *Rhaphiolepis×delacourii* Andre. Distinctive characeristics of cultivars similar to 'Georgia Petite' are presented in the following table:

| Species/ Cultivar | Leaf Shape | Leaf Size | Flower Color | Winter Hardiness* | Leaf-spot Resistance** | Plant Size Ht. × Spd. |
|---|---|---|---|---|---|---|
| *R. indica* Indian Hawthorn | Undulating | Variable | Pink | 8b (15° F.) | Poor | Variable |
| *R. umbellata* Yedda Hawthorn | Smooth | Variable | White | 8 (10° F.) | Good | Variable |
| *R.* × *delacourii* Hybrid | Variable | Variable | Lt.-Pink White | 8 (10° F.) | Poor-Good | 4 × 6 [feet] |
| *R.* × *delacourii* 'Eskimo' | Elliptic-obovate Smooth | 2.2 × 0.8 [inches] | Lt. Pink | 7b (5° F.) | Excellent | 6 × 8 [feet] |
| *R.* × *delacourii* 'Georgia Petite' | Lightly serrated Obovate | 2.3 × 1.6 [inches] | Lt. Pink | 7b (5° F.) | Excellent | 2.5 × 3 [feet] |
| *R.* × *delacourii* 'Georgia Charm' | Distally serrated Elliptic-obovate | 2.0 × 0.8 [inches] | White | 7b (5° F.) | Excellent | 4 × 5 [feet] |

*Excerpted from landscape plantings and laboratory freeze tests; USDA Plant Hardiness Zones.
**Excerpted from replicated field tests interplanted with infected susceptible species for inoculation.

The cultivar 'Georgia Petite' is an evergreen shrub which typically matures at aproximately 2.5 feet in height with a rounded canopy, spreading to approximately 3.3 feet in width. Branching is very compact, leading to the low stature of the plant, and flowering is precocious. Growth is vigorous prior to maturity and moderately slow thereafter. When grown in partial shade locations, plant measurements increase by 8 to 10 inches, but plant canopy remains very desirable and flowering remains precocious. Its flowers are light pink (R.H.S. Color 56D) fading to white at maturity with stamen color typical of the parent species. The flowers appear for two to three weeks during middle to late April in northern Georgia, although the exact flowering period is dependent on weather conditions. Flowering occurs in the first year. The leaves are dark green with light green underside and serrate margins. The leaf shape is obovate and rounded at the apex, measuring approximately 2.3 inches× 1.6 inches. New growth is whorled on stems with five to six new branches approximately two inches in length. The internode length is approximately 0.75 to 1.0 inches. Five to six leaves originate just below each terminal stem bud. The terminal stem buds are dark purplish in color. Bark on current season's growth is greenish-brown and changes to grey-brown during the second year. Clusters of bluish-black fruits (R.H.S. Color 103A) are approximately one centimeter in diameter and persist from summer into winter. The fruits are not significntly different from those of either parent but due to the compact habit of leaf and stem arrangement, the fruits are inconspicuous.

'Georgia Petite' showed no symptoms of leafspot during replicated field tests when interplanted with infected susceptible species (redtipped photinia and cleyra) for inoculation, which makes it significantly distinct from most other commercially available cultivars of this species. The cold tolerance is significantly improved, thus extending the adaptbility range of this species northward to the piedmont areas of the southeastern United States (USDA Hardiness Zone 7b). The traits of the dwarf habit, the cold tolerance, and the strong resistance to leafspot disease make this a unique selection in the species and a good companion plant for the landscape designer's plant palettes in developing environmental plantings located in USDA climactic zones 7b to 10.

I claim:

1. The new distinct plant cultivar of *Rhaphiolepis*× *delacourii* Andre, substantially as herein shown and described.

* * * * *